United States Patent [19]

Blumberg et al.

[11] Patent Number: 5,674,902
[45] Date of Patent: Oct. 7, 1997

[54] METHOD OF INHIBITING HYPERPLASIA TO A MAMMAL IN NEED THEREOF

[75] Inventors: Peter M. Blumberg, Frederick; Zoltan Szallasi, Chevy Chase, both of Md.

[73] Assignee: The United States of America as represented by the Department of Health and Human Services, Washington, D.C.

[21] Appl. No.: 452,392

[22] Filed: May 26, 1995

Related U.S. Application Data

[62] Division of Ser. No. 924,439, Jul. 31, 1992, Pat. No. 5,420,162, which is a continuation of Ser. No. 681,679, Apr. 8, 1991, abandoned.

[51] Int. Cl.$^6$ ............................ A61K 31/19; A61K 31/12
[52] U.S. Cl. ..................... 514/570; 514/691; 514/886
[58] Field of Search .......................... 514/570, 691, 514/886

[56] References Cited

U.S. PATENT DOCUMENTS

| | | | |
|---|---|---|---|
| 4,716,179 | 12/1987 | Hecker et al. | 514/691 |
| 5,420,162 | 5/1995 | Blumberg et al. | 514/570 |

OTHER PUBLICATIONS

Chemical Abstracts (118: 32646m) Szallasi et al. 1992.
Akita et al., "Expression and Properties of Two Distinct Classes of the Phorbol Ester Receptor Family, Four Conventional Protein Kinase C Types, and a Novel Protein Kinase C," *J. Biological Chemistry*, 265(1), 354–362 (Jan. 1990).
Baird et al., "Tumor–promoting Activity of Phorbol and Four Diesters of Phorbol in Mouse Skin," *Cancer Research*, 31, 1074–79 (Aug. 1971).
Berry et al., "Metabolic Conversion of 12–O–Tetradecanoylphorbol–13–acetate in Adult and Newborn Mouse Skin and Mouse Liver Microsomes," *Cancer Research*, 38, 2301–06 (Aug. 1978).
Binder et al., "Characterization of the Induction f Ornithine Decarboxylase Activity by Benzoyl Peroxide in SENCAR Mouse Epidermis," *Carcinogenesis*, 10(12), 2351–57 (1989).
Blumberg, "Protein Kinase C as the Receptor for the Phorbol Ester Tumor Promoters: Sixth Rhoads Memorial Award Lecture," *Cancer Research*, 48, 1–8 (Jan. 1988).
Blumberg et al., "Specific Receptors for Phorbol Ester Tumor Promoters and Their Involvement in Biological Responses" (Chapter 5) in *Mechanisms of Tumor Promotion* (vol. III) (Thomas J. Slaga, ed., CRC Press, Inc., Boca Raton, Florida 1984).
Campbell, "Lipid–Derived Autacoids: Eicosanoids and Platelet–Activating Factor" (Chapter 24) in *Goodman and Gilman's The Pharmacological Basis of Therapeutics*, 8th Ed. (Gilman et al., ed., Pergamon Press, New York 1990).
Casnellie, "Protein Kinase Inhibitors: Probes for the Functions of Protein Phosphorylation," *Advances in Pharmacology*, 22, 167–71 (1991).

Dunn et al., "Specific Binding of [20–$^3$H]12–Deoxyphorbol 13–Isobutyrate to Phorbol Ester Receptor Subclasses in Mouse Skin Particulate Preparations," *Cancer Research*, 43, 4632–37 (Oct. 1983).
Ellis et al., "Activation of Protein Kinase C by Tumor–Promoting and Non–Promoting Phorbol Esters," *J. Pharmacy and Pharmacology*, 37, 23P (Dec. 1985).
Fürstenberger et al., "Zum Wirkungsmechanismus Cocarcinogener Pflanzeninhaltsstoffe," *Planta Medica*, 22, 241–266 (1972).
Fürstenberger et al., "Skin Tumor Promotion by Phorbol Esters Is A Two–Stage Process," *Proc. Natl. Acad. Sci. USA*, 78(12), 7722–26 (Dec. 1981).
Goth, "Drug–Receptor Interactions" (Chapter 2) in *Medical Pharmacology Principles and Concepts*, 10th Ed. (The C.V. Mosby Company, St. Louis 1981).
Gschwendt et al., "Bryostatin 1, An Activator of Protein Kinase C, Mimics As Well As Inhibits Biological Effects of the Phorbol Ester TPA in vivo and in vitro," *Carcinogenesis*, 9(4), 555–62 (1988).
Hennings et al., "Bryostatin 1, An Activator of Protein Kinase C, Inhibits Tumor Promotion by Phorbol Esters in SENCAR Mouse Skin," *Carcinogenesis*, 8(9), 1343–46 (1987).
Hergenhahn et al., "Biological Assays for Irritant Tumor–initiating and—promoting Activities," *J. Cancer Res. Clin. Oncol.*, 104, 31–39 (1982).
Insel, "Angalgesic–Antipyretics and Antiinflammatory Agents; Drugs Employed in the Treatment of Rheumatoid Arthritis and Gout" (Chapter 26) in *Goodman and Gilman's The Pharmacological Basis of Therapeutics*, 8th Ed. (Gilman et al., ed., Pergamon Press, New York 1990).
Irie et al., "Structure—Activity Studies of the Indole Alkaloid Tumor Promoter Teleocidins," *Carcinogenesis*, 8(4), 547–552 (1987).
Klein–Szanto, "Morphological Evaluation of Tumor Promoter Effects on Mammalian Skin" (Chapter 3) in *Mechanisms of Tumor Promotion* (vol. II) (Thomas J. Slaga, ed., CRC Press, Inc., Boca Raton, Florida 1984).
Lichti et al., "Genetic Evidence That a Phorbol Ester Tumor Promoter Stimulates Ornithine Decarboxylase Activity by a Pathway That Is Independent of Cyclic AMP–Dependent Protein Kinases in CHO Cells," *J. Cellular Physiology*, 113, 433–39 (1982).

(List continued on next page.)

*Primary Examiner*—Kevin E. Weddington
*Attorney, Agent, or Firm*—Leydig, Voit & Mayer, Ltd.

[57] ABSTRACT

The present invention relates to a method of inhibiting a protein kinase C-mediated biological response, such as, hyperplasia. The method comprises administering to a mammal a non-tumor promoting 12-deoxyphorbol ester. Phorbol esters suitable for use in the method include 12-deoxyphorbol 13-monoesters wherein the ester is a formate, acetate, propionate, butyrate, pentanoate, hexanoate, benzoate or phenylacetate ester.

6 Claims, 7 Drawing Sheets

OTHER PUBLICATIONS

Madri, "Inflammation and Healing" (Chapter 2) in *Anderson's Pathology*, 9th Ed. (Kissane, ed., The C.V. Mosby Company, St. Louis 1990).

Nishizuka, "The Role of Protein Kinase C in Cell Surface Signal Transduction and Tumour Promotion," *Nature*, 308(19), 693–98 (Apr. 1984).

Nishizuka, "Studies and Perspectives of Protein Kinase C," *Science*, 233, 305–12 (Jul. 1986).

Nishizuka, "Studies and Prospectives of the Protein Kinase C Family for Cellular Regulation," *Cancer*, 63, 1892–1903 (May 1989).

Nishizuka, "The Molecular Heterogeneity of Protein Kinase C and Its Implications for Cellular Regulation," *Nature*, 334(25), 661–65 (Aug. 1988).

O'Brien et al., "Induction of the Polyamine–biosynthetic Enzymes in Mouse Epidermis by Tumor–promoting Agents," *Cancer Research*, 35, 1662–70 (Jul. 1975).

Sako et al., "Partial Parallelism and Partial Blockade by Bryostatin 1 of Effects of Phorbol Ester Tumor Promoters on Primary Mouse Epidermal Cells," *Cancer Research*, 47, 5445–50 (Oct. 1987).

Schmidt et al., "Simple Phorbol Esters as Inhibitors of Tumor Promotion by TPA in Mouse Skin," in *Carcinogenesis and Biological Effects of Tumor Promoters*, 7, 57–63 (Hecker et al., eds., Raven Press, New York 1982).

Scribner et al., "Inflammation and Tumor Promotion: Selective Protein Induction in Mouse Skin by Tumor Promoters," *J. Cancer*, 8, 617–621 (1972).

Sekiguchi et al., "Three Distinct Forms of Rat Brain Protein Kinase C: Differential Response to Unsaturated Fatty Acids," *Biochemical and Biophysical Research Communications*, 145(2), 797–802 (Jun. 1987).

Slaga et al., "Studies on the Mechanism of Skin Tumor Promotion: Evidence for Several Stages in Promotion," *Proc. Natl. Acad. Sci. USA*, 77(6), 3659–3663 (Jun. 1980).

Slaga et al., "Overview of Tumor Promotion in Animals," *Environmental Health Perspective*, 50, 3–14 (1983).

Stanley et al., "Mouse Skin Inflammation Induced by Multiple Topical Applications of 12–O–Tetradecanoylphorbol–13–Acetate," *Skin Pharmacol.*, 4, 262–71 (1991).

Szallasi et al., "Prostratin, a Nonpromoting Phorbol Ester, Inhibits Induction by Phorbol 12–Myristate 13–Acetate of Ornithine Decarboxylase, Edema, and Hyperplasia in CD–1 Mouse Skin," *Cancer Research*, 51, 5355–60 (Oct. 1991).

Verma et al., "Induction of Mouse Epidermal Ornithine Decarboxylase Activity and DNA Synthesis by Ultraviolet Light," *Cancer Research*, 39, 1035–40 (Mar. 1979).

Yeh et al., "Influence of Side Chains on Phorbol Ester Binding to Protein Kinase C," *Chemical Abstracts*, 109, 88635p (1988).

Young et al., "Tachyphylaxis in 12–O–Tetradecanoylphorbol Acetate–and Arachidonic Acid–Induced Ear Edema," *J. Investigative Dermatology*, 80, 48–52 (1983).

Zayed et al., "Structure Activity Relations of Polyfunctional Diterpenes of the Tigliane Type, VI," *Planta Medica*, 1, 65–69 (Feb. 1984).

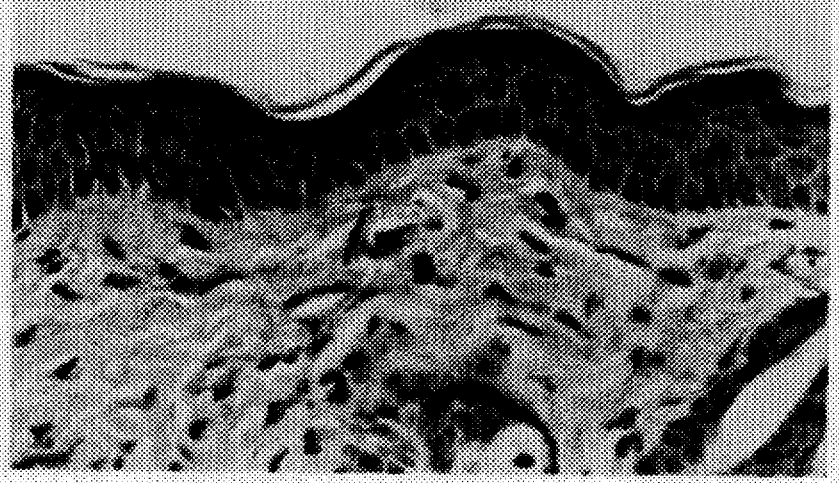
FIG. IC
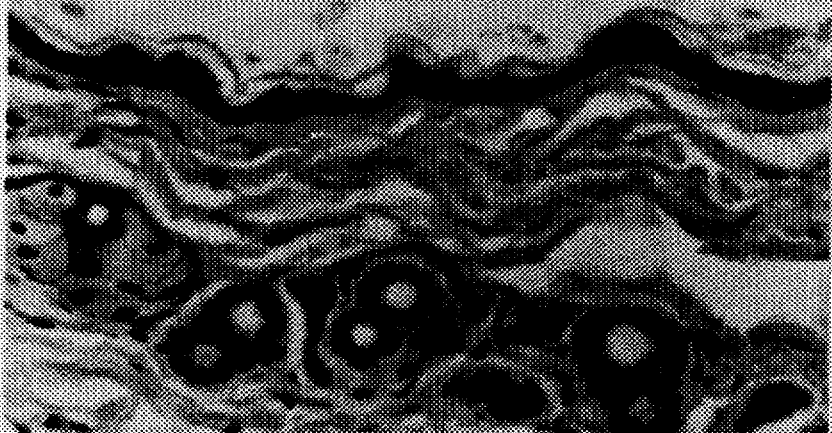
FIG. ID

METHOD OF INHIBITING HYPERPLASIA TO A MAMMAL IN NEED THEREOF

This is a divisional of application Ser. No. 07/924,439, filed on Jul. 31, 1992, now U.S. Pat. No. 5,420,162, which, in turn, is a continuation of application Ser. No. 07/681,679, filed on Apr. 8, 1991, now abandoned.

BACKGROUND OF THE INVENTION

1. Field of the Invention

The present invention relates to a method of inhibiting protein kinase C function and to compounds and compositions suitable for use in such a method.

2. Background Information

In mouse skin, phorbol esters exert tumor promoting, inflammatory, and hyperplastic activity. These responses are thought to be mediated via the major phorbol ester receptor, protein kinase C (Nishizuka, Nature, 308:693–698, 1984; Nishizuka, Science, 233:305–312, 1986; Nishizuka, Nature, 334:661–665, 1988; Blumberg et al, In: T. J. Slaga (ed.) Mechanisms of Tumor Promotion, Tumor Promotion and Carcinogenesis In Vitro, vol. 3, pp. 143–184, Boca Raton, Fla.: CRC Press, 1984).

Using [$H^3$]PDBu, Blumberg and co-workers characterized specific, high-affinity phorbol ester binding sites in particulate preparations from mouse skin and mouse epidermis. The measurements yielded curved Scatchard plots, consistent with receptor heterogeneity (Dunn et al, Cancer Res., 43:4632–4637, 1983). These were the first results suggesting that the phorbol ester receptors, subsequently identified as PKC, might represent a family of isoforms differing in structure-activity relations. It is now known that protein kinase C indeed consists of at least 9 isozymes (Blumberg, Cancer Res., 48:1–8, 1988; Nishizuka, Cancer 63:1982–1903, 1989). The binding characteristics of only the alpha, beta, and gamma isozymes have been investigated in detail so far. These three isozymes appear quite similar for recognizing the phorbol esters, although differences in interaction with unsaturated fatty acids have been noted (Sekiguchi et al, Biochem. Biophys. Res. Commun., 145:797–802, 1987; Akita et al, J. Biol. Chem., 265:354–362, 1990).

Despite the lack of biochemical understanding, whole animal analysis argues strongly for heterogeneity in response to the phorbol esters. A decade ago, Hecker and co-workers demonstrated that 12-deoxyphorbol 13-phenylacetate, -isobutyrate, or -angelate were inflammatory but either not promoting or weakly promoting (Hergenhahn et al, J. Cancer Res. Clin. Oncol., 104:31–39, 1982). Similar behavior was noted for phorbol esters with unsaturated side chains (Furstenberger et al, Planta Medica, 22:241–266, 1972). The groups of Slaga (Proc. Natl. Acad. Sol. USA, 77:3659–3663, 1980; Slaga Environ. Health Perspect., 50:3–14, 1983) and Marks (Proc. Natl. Acad. Sci. USA, 78:7722–7726, 1981) showed that tumor promotion could be subdivided into distinct stages differing in structure-activity requirements; mazerein and 12-O-retinoylphorbol 13-acetate, although only weakly promoting themselves, were effective if preceded by one or more applications of phorbol 12-myristate 13-acetate (PMA).

In all of the above cases, the compounds induce in cultured cells essentially the complete spectrum of phorbol ester responses. This is not so for the bryostatins, a structurally distinct class of protean kinase C activators. The bryostatins induce only some of the responses seen for the phorbol esters; when co-applied with the phorbol esters, the bryostatins block those responses which they themselves do not induce (Blumberg, Cancer Res., 48:1–8, 1988). In mouse keratinocytes, the bryostatins fail to induce markers of differentiation (Sako et al, Cancer Res., 47:5445–5450, 1987). In mouse skin, the bryostatins are inactive as first stage promoters (Gschwendt et al, Carcinogenesis, 9:555–562, 1988), very weak as second stage promoters or as complete promoters (Hennings et al, Carcinogenesis, 8:1343–1346, 1987), strong inhibitors of first stage promotion (Gschwendt et al, Carcinogenesis, 9:555–562, 1988), and modest inhibitors of complete promotion (Hennings et al, Carcinogenesis, 8:1343–1346, 1987).

One other report of protein kinase C activators which inhibit tumor promotion remains difficult to evaluate. Schmidt and Hecker (In: E. Hecker, N. E. Fusenig, W. Kunz, F. Marks and H. W. Thielmann (eds.) Cocarcinogenesis and Biological Effects of Tumor Promoters, pp. 57–63. New York: Raven Press, 1982) reported that co-application of PMA and a 4- to 8-fold higher dose of phorbol 12,13-diacetate, -dibutyrate, -dipropionate, or -dibenzoate completely blocked promotion in NMRI mice. This was clearly not seen for phorbol 12,13-diacetate in SENCAR mice (Slaga et al, Proc. Natl. Aced. Sci. USA, 77:3659–3663, 1980, and phorbol 12,13-dibutyrate and phorbol 12-13-dibenzoate are themselves tumor promoting (Scribner et al, Europ. J. Cancer, 8:617–621, 1972; Baird et al, Cancer Res., 31:1074–1079, 1971). In the same paper, Schmidt and Hecker also reported that a single co-treatment had no effect on thymidine incorporation or hyperplasia in NMRI mouse skin and that, after eight cotreatments, there was only a slightly less intense hyperplasia than after eight treatments with PMA alone.

Applicants have characterized the biological effects of 12-deoxyphorbol 13-acetate (prostratin). Specifically, Applicants have examined the effect of single or multiple pretreatments of mouse skin with prostratin on the subsequent response to PMA. The results indicate that prostratin pretreatment inhibits the response to PMA, with varying characteristics for different responses. Prostratin thus represents a novel class of physiological antagonist for protein kinase C.

SUMMARY OF THE INVENTION

The present invention is based on Applicants' discovery that certain phorbol-related diterpene esters lacking tumor promoting activity possess antihyperplastic activity and anti-inflammatory activity. Accordingly, the invention relates to a method of using these esters to block these and other such protein kinase C-mediated responses.

It is an object of the invention to provide a method of treating disorders involving the protein kinase C pathway.

It is a further object of the invention to provide novel phorbol-related diterpene esters suitable for use in the above-described method, and to provide pharmaceutical compositions containing same.

Further objects and advantages of the present invention will be clear from the description that follows.

BRIEF DESCRIPTION OF THE DRAWINGS

FIG. 6. Effect of prostratin on hyperplasia and inflammation induced by PMA.

DETAILED DESCRIPTION OF THE INVENTION

Figure 1A:
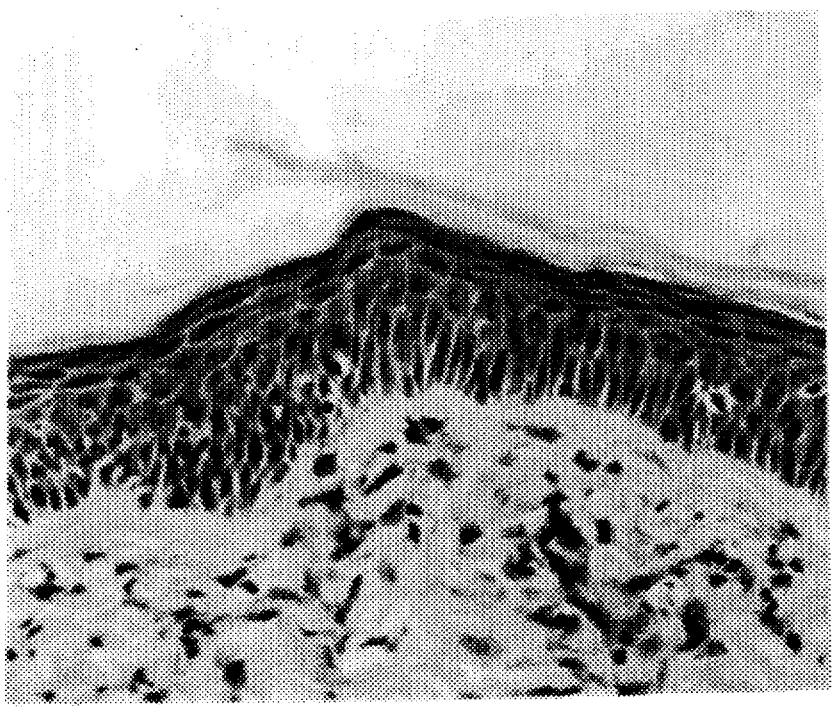
FIG. 1. The effect of prostratin pretreatment on the morphological changes of back skin induced by PMA. Mice were treated by the following protocols: A) 100 μl acetone at 0 and 48 hrs and 10 μg PMA 15 min later. B) 1 mg prostratin at 0 and 48 hrs and 10 μg PMA 15 min later. C) 0.1 mg prostratin at 0 and 48 hrs and 10 μg PMA 15 min later. D) 0.1 mg prostratin at 0 hr, 1 mg prostratin at 48 hrs and 10 µg PMA 15 min later. Mice were sacrificed 72 hrs after the last treatment. All compounds were applied in 100 µl acetone. (400 X).

The present invention relates to a method of using a class of phorbol related diterpenes to inhibit protein kinase C function and thereby to block biological responses mediated by protein kinase C, including hyperplasia, inflammation and edema. The invention further relates to novel compounds within this class and to pharmaceutical compositions comprising same.

Compounds suitable for use in the method to which the invention relates are 12-deoxyphorbol 13-monoesters wherein the ester can be a formate, acetate, propionate, butyrate, pentanoate, hexanoate, benzoate or phenylacetate ester.

These compounds can be used to treat two classes of disorders involving the protein kinase C pathway. First, they can be used to treat those conditions mediated by protein kinase C that fall in the subclass of responses which they block. These would include: inflammatory dermatoses such as psoriasis, seborrheic dermatitis, chloracne, atopic dermatitis, allergic contact dermatitis, lichen simplex chronicus, eczematous dermatitis, erythema multiforme, cutaneous lupus erythematosus, and panniculitis. Likewise, they can be used as anti-inflammatory agents in general for treatment of subacute and chronic inflammation, as well as in immune suppression following transplantation or autoimmune disease. A partial list of such conditions includes vasculitis, chronic bronchitis, chronic glomerulonephritis, chronic gastritis, Crohn's disease, chronic hepatitis and pancreatitis, prostatitis, thyroiditis, rheumatoid arthritis, and myositis.

Second, these compounds can be used as protein kinase C agonists for those responses that they do not block, but where the tumor promoting and inflammatory activities of the usual phorbol esters represent unacceptable toxicity. These responses include use as drugs for treatment of leukemia or melanoma, acting through their ability to induce differentiation.

The novel 12-deoxyphorbol derivatives to which the invention relates are 12-deoxphorbol 13-monoesters wherein the ester can be a formate, propionate, butyrate or pentanoate ester. Synthesis of the propionate ester is set further in Example 5. Based on that disclosure, and knowledge of the art, an artisan could readily synthesis the other members of this group of novel derivatives.

Pharmaceutical compositions of the present invention comprise, as an active ingredient, at least one of the known or novel phorbol derivatives described above, together with a pharmaceutically acceptable carrier. The active ingredient is present in the composition in an amount sufficient to produce the desired effect (e.g. anti-inflammatory, anti-hyperplastic, etc). The composition of the invention can be formulated so as to be suitable for human or for veterinary use.

Preferably, the pharmaceutical composition of the invention includes the active ingredient in a quantity selected from 0.01 µg to 10 gm, advantageously, from about 10 µg to 10 mg, per dosage unit, depending on the specific derivative and route of administration. Appropriate concentrations and dosage unit sizes can be readily determined by one skilled in the art.

Pharmaceutical carriers suitable for use in the composition to which the invention relates include, but are not limited to, injectable or orally or rectally administerable oils, lipid emulsions or aqueous suspensions, or in the case of orally or rectally administerable tablets or capsules, a pharmacologically inert excipient.

As indicated above, the pharmaceutical composition of the invention can be present in dosage unit form. For example, the composition can take the form of a tablet, capsule, inhalant, syrup, emulsion, gel, ointment, cream, lotion, transdermal patch, suppository, sterile injectable liquid as well as a liquid suspension or solution. The pharmaceutical composition of the present invention can be prepared by conventional techniques.

The method of treatment to which this invention relates comprises administering to a subject in need of such treatment an amount of at least one of the above-noted known or novel phorbol derivatives sufficient to produce the desired effect. The derivatives can be administered orally, nasally, topically, transdermally, parenterally or anally, as may be required to achieve the desired effect. One skilled in the art can readily determine the appropriate protocol to be used depending on the treatment required, (eg, anti-inflammatory, antihyperplastic, etc).

Specific aspects of the invention are described in further detail in the non-limiting Examples that follow.

EXAMPLES

Animals used in the studies referenced in the specific Examples that follow were female Charles River CD-1 mice, 6–8 weeks of age, which were obtained from Charles River Laboratories, Wilmington, Mass. The dorsal hair of each mouse was shaved 2 days before starting the treatments, and only those mice showing no hair regrowth were used. All compounds were dissolved in acetone and applied in a volume of 100 μl. Prostratin, PMA and (−)-7-octylindolactam V (OILV) were purchased from LC Services (Woburn, Mass).

Example 1

The Effects of Prostratin Pretreatment on PMA-Induced Hyperplasia

For examination of hyperplasia, dorsal skin was removed and fixed in 10% formalin in 0.1M sodium phosphate buffer, pH 7.5. It was then sectioned and stained with hematoxylin-eosin by American Histolabs, Gaithersburg, Md. Under each set of conditions in each experiment, two animals were treated, two portions of the treated skin were excised per animal, and three sections were prepared from each portion of skin.

Figure 1B:
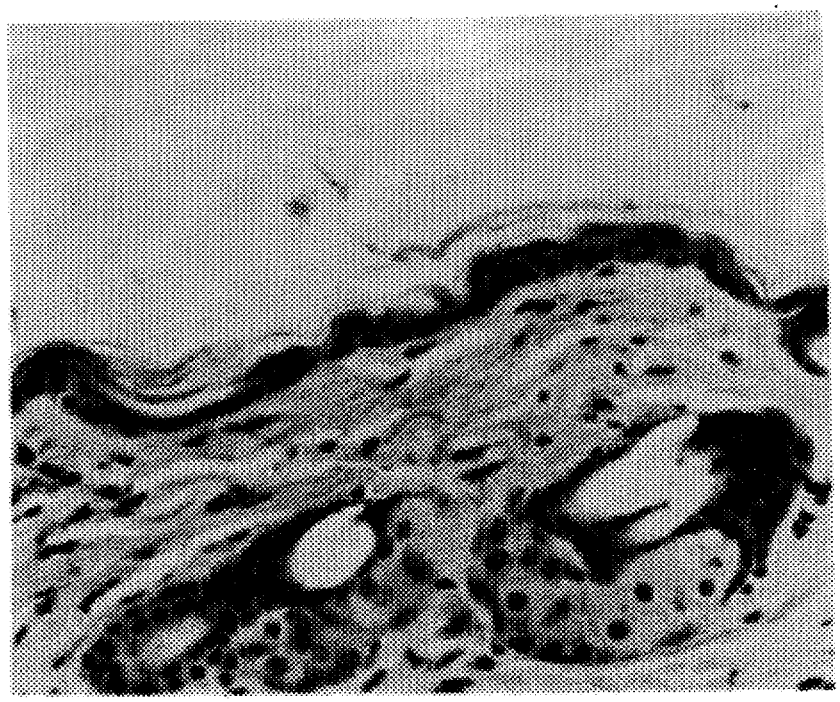

10 μg PMA induced strong hyperplasia on the backskin of CD-1 mice at 48–72 hrs after treatment (FIG. 1A). The hyperplasia could be inhibited dramatically if the animals were pretreated with prostratin at an appropriate dose and an appropriate treatment schedule. The inhibitory effect of 1 mg prostratin applied at 0 and 48 hrs on the hyperplasia induced by 10 μg PMA treatment 15 min after the second prostratin application is illustrated in FIG. 1B.

Within the severe limits imposed by the supply of prostratin, the influence of the treatment conditions on the inhibition of the PMA-induced hyperplasia was examined. Using 3 applications of prostratin at 48 hr intervals, followed by 10 μg PMA at 48 hrs after the last prostratin application, 1 mg prostratin was effective but 0.1 mg or lower doses failed to inhibit. Six applications of 1 mg prostratin was likewise effective, whereas a single dose of 1 mg prostratin, followed by 10 μg PMA at 15 min to 7 days after the prostratin application, failed to inhibit hyperplasia. Following 2 applications of prostratin separated by 48 hr, hyperplasia was substantially inhibited for applications of 10 μg PMA 15 min to 6 hr after the last prostratin application, partially restored at 48 h and largely recovered by 96 hr. When the interval between the two applications of 1 mg prostratin was varied, with challenge with 10 μg PMA 15 min after the last prostratin application, inhibition was most effective for intervals of 24 hrs to 8 days.

Because prostratin was more potent for inhibiting ODC induction than for blocking hyperplasia (see below), combinations of a lower dose of prostratin followed by a higher dose were also examined. Interestingly, although two applications of 0.1 mg prostratin at an interval of 48 hr failed to inhibit hyperplasia to 10 μg PMA applied 15 min after the second application (FIG. 1C), the inhibition was complete for a first dose of 0.1 mg prostratin, provided the second dose was 1 mg (FIG. 1D).

The inhibition of hyperplasia induced by PMA depended not only on the dose of prostratin but also on the dose of PMA evaluated. In control mice, 100 μg of PMA caused substantial necrosis in addition to hyperplasia. The hyperplasia induced by 100 μg PMA was not blocked under the usual protocol of two pretreatments with 1 mg prostratin, but the necrosis was largely prevented.

Example 2

The Effect of Prostratin Pretreatment on PMA-Induced ODC Activity

For analysis of ornithine decarboxylase activity, the epidermis of individual mice was separated from the dermis by brief heat treatment (O'Brien et al, Cancer Res., 35:1662–1670, 1975). The epidermal preparations of 2 mice were pooled and then homogenized for 20 sec at 0°–4° C. in 50 mM sodium phosphate buffer, pH 7.2, containing 0.1 mM pyridoxal phosphate and 0.1 mM ethylenediaminetetraacetic acid (O'Brien et al, Cancer Res., 35:1662–1670, 1975) using a Polytron tissue homogenizer. The supernatant fraction obtained after centrifugation at 30,000 × g for 2 ×20 min at 0° C. was used for determination of enzymatic activity, quantitated by the release of $CO_2$ from L-$^{16}$C-ornithine (Amersham, Arlington Heights, Ill. and Dupont NEN, Boston, Mass.) as described by Lichti and Gottesman (J. Cell. Physiology, 113:433–439, 1982). In animals treated with solvent only the $CO_2$ release was under 0.1 nmole $CO_2$/mg protein/hour.

Figure 2:
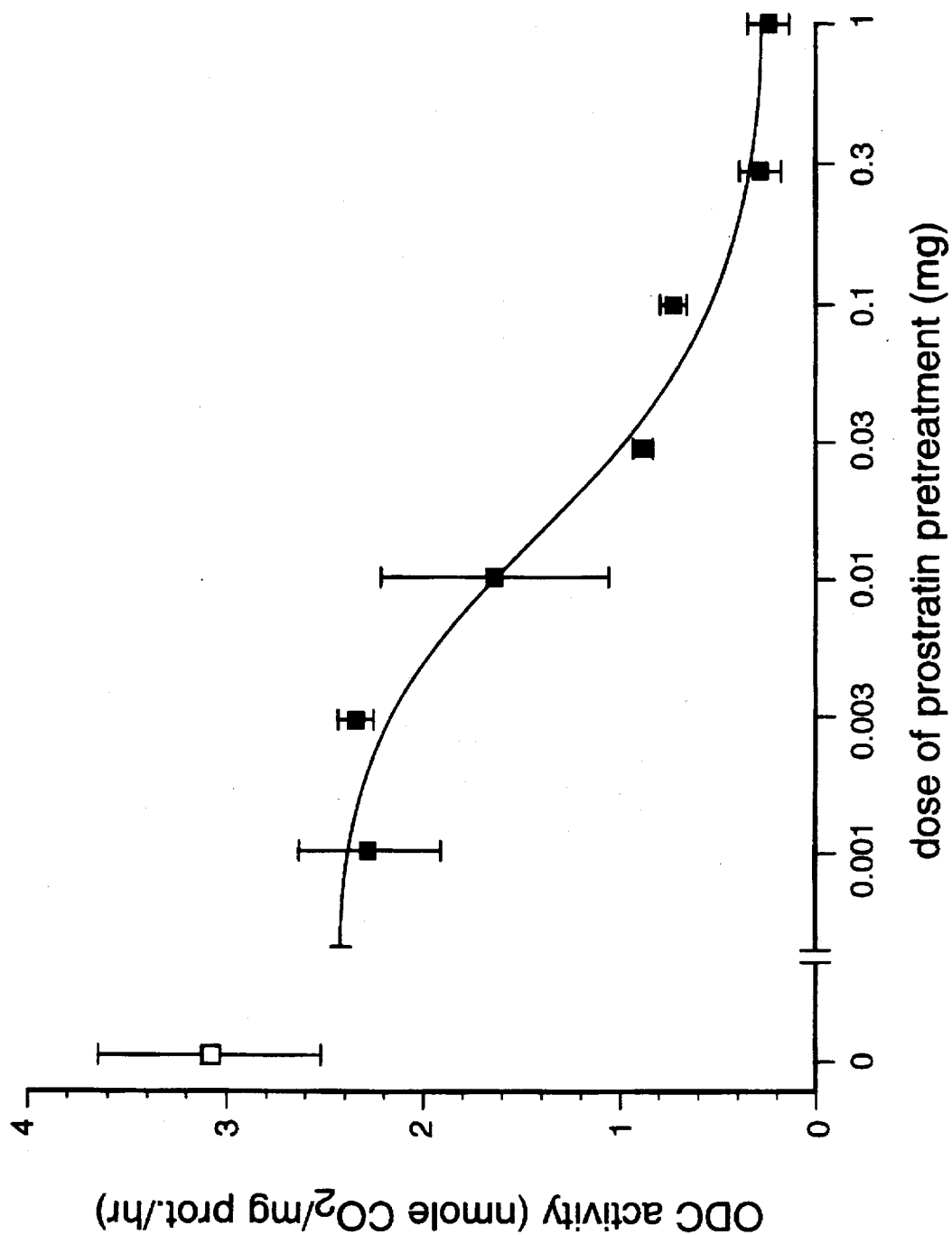
FIG. 2. Dose dependent inhibition of PMA induced ornithine decarboxylase (ODC) activity by multiple prostratin pretreatments. Six per group were treated with the indicated doses of prostratin (■) 3 times at 48 hr intervals. Forty-eight hrs after the last pretreatment 10 µg PMA were applied to the back skin and the ODC activity of preparations derived from two pooled skins was measured 6 hrs later. Each value represents the average ± S.E.M. Control animals were pretreated with solvent only (□).
Figure 3:
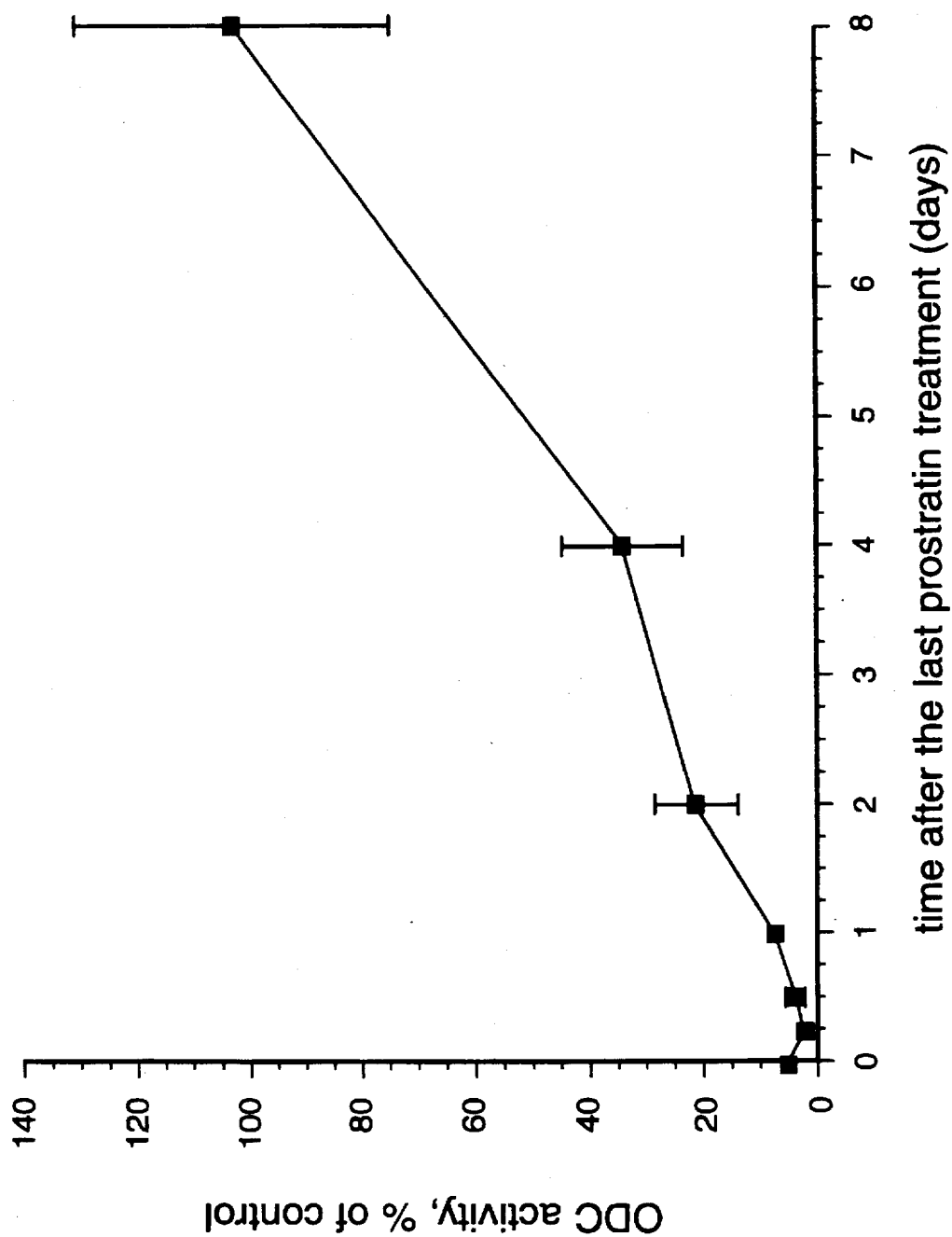
FIG. 3. The recovery of ODC inducibility after prostratin pretreatment. Six mice per group were treated with 100 µg prostratin (■) 3 times at 48 hr intervals. Fifteen min, 6, 12, 24 hrs, 2, 4, and 8 days after the last pretreatment 10 µg PMA were applied to the back skin and the ODC activity of preparations derived from two pooled skins was measured 6 hrs later. The results were expressed as percentages of the control values derived from mice pretreated with solvent only. Data representing the same time points in three independent experiments were pooled. Each value represents the average ± S.E.M. All compounds were applied in 100 µl acetone.

It had been previously observed that a single treatment with prostratin itself induced ODC, but the maximal induction was only 25–30% of that induced by 10 μg PMA and the peak of induction as a function of time was broader. Pretreatment with 100 μg prostratin inhibited the induction of ODC by 10 μg PMA applied 48 hrs after the prostratin. Inhibition by a single prostratin application was greater than 60%; that by 2 to 6 applications at 48 hr intervals was 90–98% (Table 1). The dose response curve for prostratin inhibition was determined using three treatments at 48 hr intervals. The $ID_{50}$ was 10 μg (FIG. 2), markedly lower than the effective dose for inhibition of hyperplasia. Conversely, the time course for recovery from inhibition after three treatments with 100 μg prostratin was slower than for inhibition of hyperplasia (FIG. 3). Substantial inhibition remained at 4 days and full recovery was only found at 8 days.

TABLE 1

The effect of number of prostratin pretreatments on the ODC inducibility by PMA
4–6 mice per group were treated with 100 μg prostratin as many times as indicated at 48 hr intervals. 48 hrs after the last pretreatment 10 μg PMA was applied and the ODC activity of preparations derived from two pooled skins was measured 6 hrs later. Each value represents the average +/− range or S.E.M. All compounds were applied in 100 μl acetone.

| Number of prostratin pretreatments | ODC activity induced by 10 μg PMA 48 hrs after the last prostratin treatment (nmol $CO_2$/hr/mg treatment) | |
|---|---|---|
| (100 μg) | Experiment 1 | Experiment 2 |
| 0 | 1.76 +/− 0.13 | 4.59 +/− 0.96 |
| 1 | 0.72 +/− 0.15 | 0.56 +/− 0.20 |
| 2 | 0.20 +/− 0.02 | 0.50 +/− 0.16 |
| 3 | 0.25 +/− 0.06 | 0.20 +/− 0.09 |
| 6 | 0.21 +/− 0.02 | 0.18 +/− 0.07 |

Figure 4:
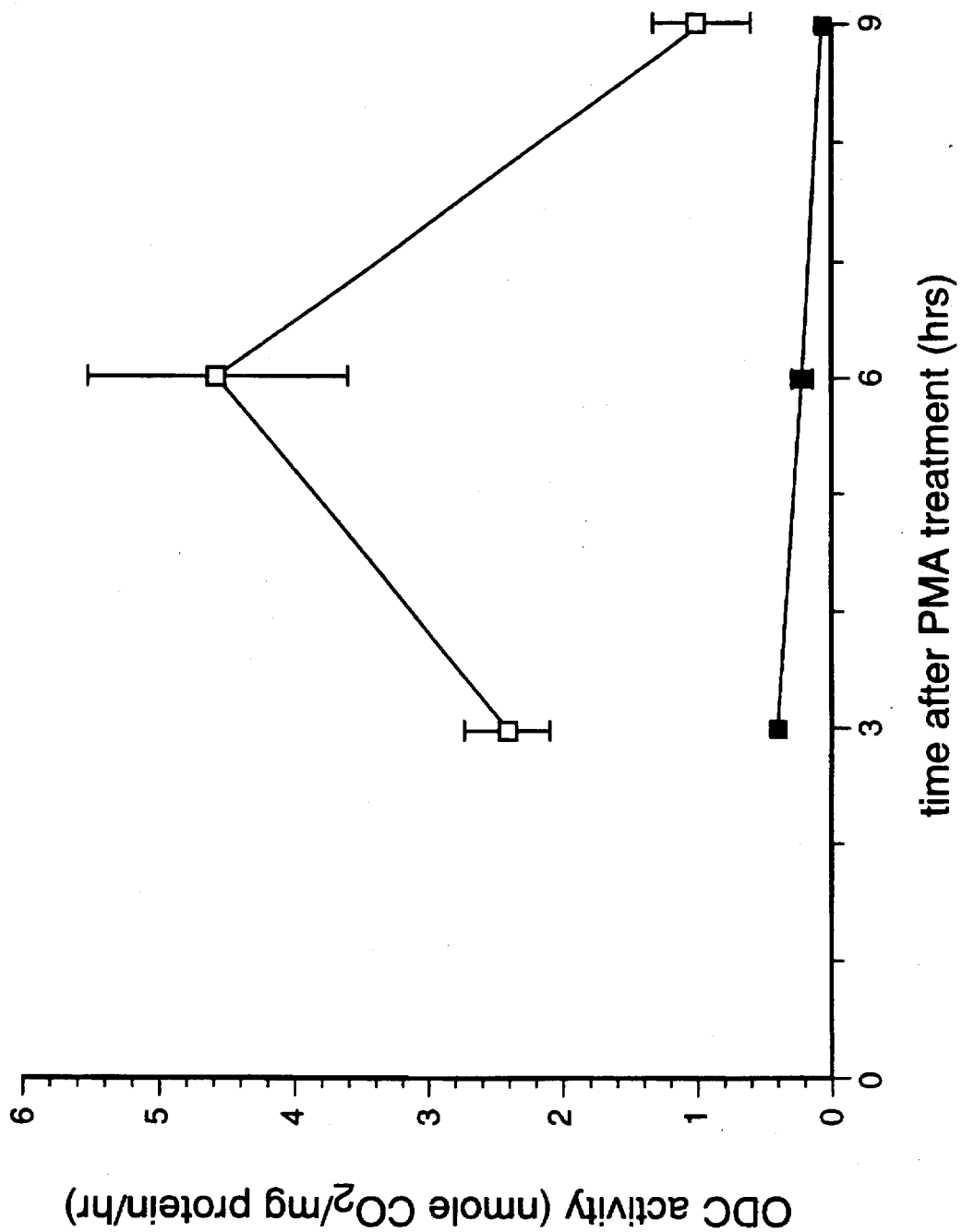
FIG. 4. Time dependence of the induction of ODC activity by PMA after prostratin or solvent only pretreatment. Six mice per group were treated with 100 µg prostratin (■) or solvent only (□) 3 times at 48 hr intervals. Forty eight hrs after the last pretreatment 10 µg PMA was applied to the back skin and the ODC activity of preparations derived from pooled skins was measured 3,6, and 9 hrs later. Each value represents the average ± S.E.M. All compounds were applied in 100 µl acetone.

Since different agents can induce ODC with substantially different time courses (Binder et al, Carcinogenesis, 10:2351–2357, 1989; Verma et al, Cancer Res., 39:1035–1040, 1979), whether there was any time shift caused by the prostratin pretreatment was checked. FIG. 4 shows that the pretreated animals 3, 6 and 9 hrs after PMA treatment showed no significant elevation of ODC activity.

To exclude the possibility that the inhibition by prostratin resulted from enhanced metabolism of PMA, the effect on another potent PKC activator of a different structural class was examined. OILV, a teleocidin analog (Irie et al, Carcinogenesis, 8:547–552, 1987), lacks the ester residues of PMA which are cleaved during metabolic breakdown (Berry et al, Cancer Res., 38:2301–2306, 1978). The ODC activity induced by 10 µg (−)-7-octylindolactam (4.9±0.8 and 7.32 ±3.89 nmol $CO_2$/hr/mg protein in two independent experiments) was several-fold higher than that induced by 10 µg PMA but prostratin pretreatment again was inhibitory (1.11±0.17 and 0.62±0.04 nmol $CO_2$/hr/mg protein, respectively).

Example 3

The Effect of Prostratin Pretreatment on PMA-Induced Back Skin Edema

For measurement of edema, skins were removed after cervical dislocation, and 0.6 cm punches were cut out and quickly weighed. The skin punches were dried for 24 hr at 60° C. and then reweighed. Data were expressed as the ratio of the water content (wet minus dry weight)/dry weight of each skin punch.

Figure 5:
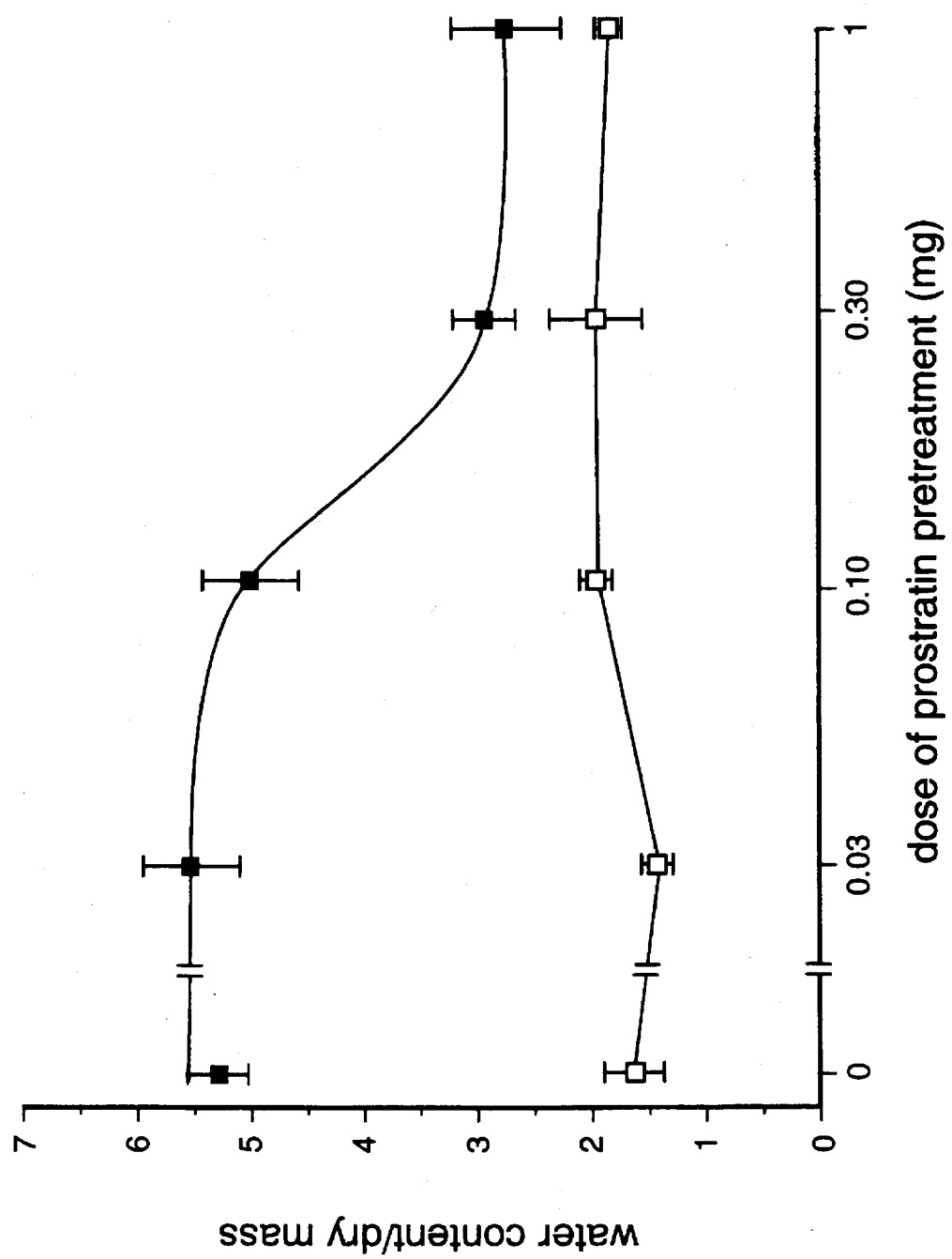
FIG. 5. Dose dependent reduction of PMA induced edema by multiple prostratin pretreatments. Six mice per group were treated with the indicated doses of prostratin 3 times at 48 hrs intervals. 48 hrs after the last pretreatment 10 µg PMA (■) or solvent (□) was applied to the back skin and 6 hrs later skin punches of 0.6 cm diameter were removed. Edema is expressed as the ratio of the water content/dry mass where the water content is the difference between the wet and dry weight. Each point represents the average of 6 animals ± S.E.M.

Prostratin pretreatment reduced the level of edema induced by 10 µg PMA in a dose-dependent manner (FIG. 5). Because of limitations on the amount of prostratin, it was not possible to determine whether complete inhibition could be achieved if the dose were further increased beyond 1 mg.

Example 4

Suppression of Inflammatory Activity by Prostratin

Figure 6A:
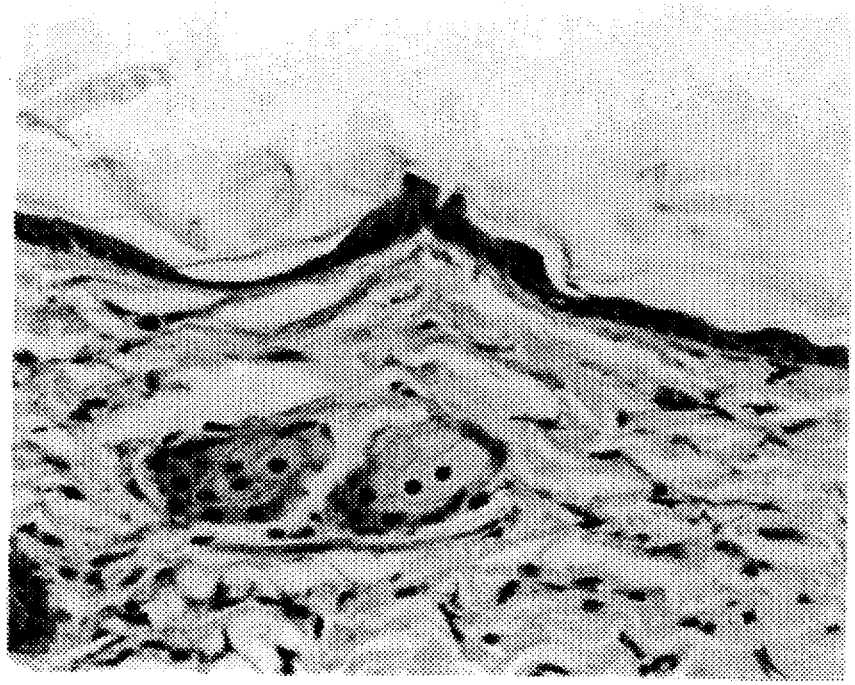
FIG. 6A: Prostratin-treated.
Figure 6B:
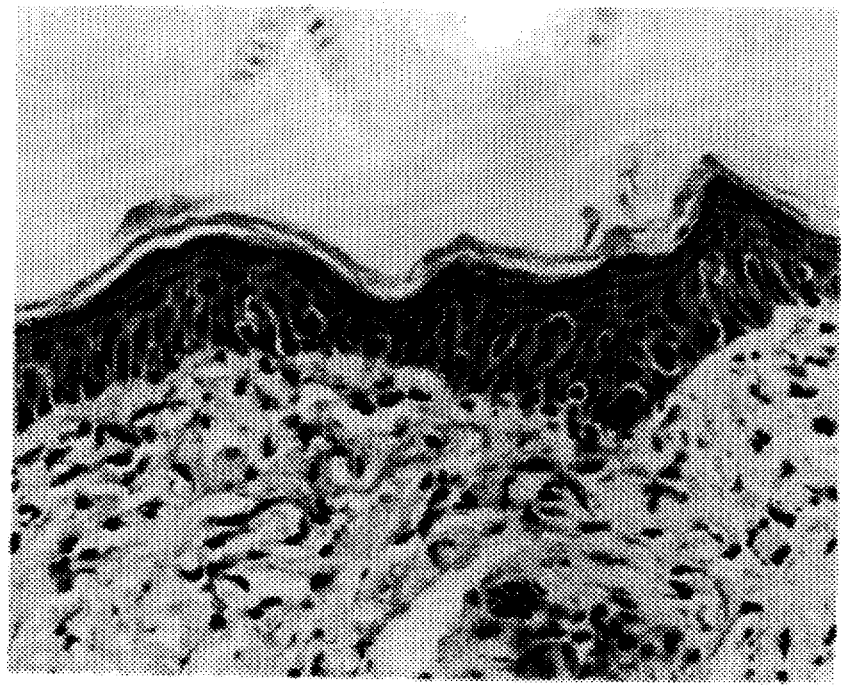
FIG. 6B: control.

CD-1 mice are treated with 100 µg prostratin applied in 100 µl acetone to the shaved back skin. Starting 48 hrs later, the animals are treated 5 times at 48 hr intervals with 1 mg prostratin and 15 min later with 2 µg phorbol 12-myristate 13-acetate (FIG. 6A). Control animals are treated in the same fashion, except that the treatments with prostratin in acetone are performed with acetone alone (FIG. 6B). The presence of infiltrating inflammatory cells can be clearly seen in FIG. 6B and missing in FIG. 6A.

Example 5

Synthesis of Novel 12-Deoxyphorbol Ester 12-deoxyphorbol 13-propionate is prepared as follows: 20 mg of 12-deoxyphorbol 20-p-methoxytrityl ether (32.2 µmol) is dissolved in 2.5 ml methylene chloride and 2.5 ml pyridine is added. The sample is chilled and a 6-fold excess of propionyl chloride (186 µ mol) in 2.5 ml methyl chloride is added with stirring. The reaction is allowed to warm to room temperature and proceed overnight. Five ml of water is then added and the reaction allowed to sit for an additional 24 hours. It is extracted twice with methylene chloride and the methylene chloride fractions are combined. The combined methylene chloride fractions are extracted with 1N hydrochloric acid until the aqueous solution is acidic. The methylene chloride fractions are then extracted with 5% potassium bicarbonate followed by water. They are dried down on the rotary evaporator. Ten ml methanol containing 34 µl perchloric acid is added and stirred for 45 min. One ml buffer is added. It is extracted twice with methylene chloride and dried down. Finally it is purified by chromatography on HPLC using a C-18 reverse phase column and elution with 65% methanol in water.

All publications mentioned hereinabove are hereby incorporated by reference.

While the foregoing invention has been described in some detail for purposes of clarity and understanding, it will be appreciated by one skilled in the art from a reading of this disclosure that various changes in form and detail can be made without departing from the true scope of the invention.

What is claimed is:

1. A method of inhibiting hyperplasia comprising administering to a mammal in need thereof an effective amount of a 12-deoxyphorbol 13-monoester.

2. The method of claim 1, wherein said ester is selected from the group consisting of formate, acetate, propionate, butyrate, pentanoate, hexanoate, benzoate and phenylacetate.

3. The method of claim 2, wherein said ester is acetate.

4. The method of claim 2, wherein said ester is phenylacetate.

5. The method of claim 1, wherein said 12deoxyphorbol ester is administered with a pharmaceutically acceptable carrier.

6. The method of claim 1, wherein said hyperplasia is dependent upon a protein kinase C-mediated biological response.

* * * * *